(12) United States Patent
Qu et al.

(10) Patent No.: US 12,011,599 B2
(45) Date of Patent: Jun. 18, 2024

(54) DUAL-MODULE MOTION DETECTION SYSTEM FOR THE POWER SAVING OF RATE ADAPTION ALGORITHM IN LEADLESS PACEMAKER

(71) Applicant: BIOTRONIK SE & Co. KG, Berlin (DE)

(72) Inventors: Min Qu, Wilsonville, OR (US); Andrew B. Kibler, Lake Oswego, OR (US); Christopher S. de Voir, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 498 days.

(21) Appl. No.: 17/288,240

(22) PCT Filed: Sep. 11, 2019

(86) PCT No.: PCT/EP2019/074151
§ 371 (c)(1),
(2) Date: Apr. 23, 2021

(87) PCT Pub. No.: WO2020/088825
PCT Pub. Date: May 7, 2020

(65) Prior Publication Data
US 2021/0387009 A1    Dec. 16, 2021

Related U.S. Application Data

(60) Provisional application No. 62/752,384, filed on Oct. 30, 2018.

(51) Int. Cl.
*A61N 1/365* (2006.01)
*A61N 1/02* (2006.01)

(52) U.S. Cl.
CPC ......... *A61N 1/36542* (2013.01); *A61N 1/025* (2013.01); *A61N 1/36535* (2013.01)

(58) Field of Classification Search
CPC ................ A61N 1/36542; A61N 1/025; A61N 1/36535; A61N 1/3756; A61B 5/1118; A61B 2562/0219
See application file for complete search history.

(56) References Cited

U.S. PATENT DOCUMENTS

2004/0116819 A1  6/2004 Alt
2011/0208260 A1* 8/2011 Jacobson ............. A61N 1/3727
                                                   607/30
(Continued)

FOREIGN PATENT DOCUMENTS

EP   2471452 A1  7/2012
WO  2015112603 A1  7/2015

OTHER PUBLICATIONS

American Heart Association Recommendations for Physical Activity in Adults and Kids, https://www.heart.org/en/healthy-living/fitness/fitness-basics/aha-recs-for-physical-activity-in-adults, retrieved on Apr. 21, 2021, pp. 1-4.

(Continued)

*Primary Examiner* — Mallika D Fairchild
(74) *Attorney, Agent, or Firm* — Buchanan Ingersoll & Rooney PC (57) ABSTRACT

An implantable cardiac pacemaker, wherein the pacemaker is configured to apply pacing pulses to the heart of a person during operation of the pacemaker, and wherein the pacemaker comprises a motion detection system that comprises a first module and a second module. The first module is configured to continuously run during operation of the pacemaker. The second module is configured to receive a trigger signal to change from an idle state to an active state or to receive a further trigger signal to change from an active (Continued)

state to an idle state. An energy consumption per time unit of the second module in the active state is larger than in the idle state. When the second module is in its active state, the second module is configured to execute a rate adaptation algorithm that adapts a rate of the pacing pulses to meet a metabolic demand of the person.

14 Claims, 4 Drawing Sheets

(56) References Cited

U.S. PATENT DOCUMENTS

| | | |
|---|---|---|
| 2016/0242654 A1 | 8/2016 | Quinlan et al. |
| 2017/0056664 A1* | 3/2017 | Kane ..................... A61N 1/3756 |
| 2018/0184698 A1* | 7/2018 | Arne ....................... A23P 20/19 |

OTHER PUBLICATIONS

Analog Devices: "3-Axis, 2 g/ 4 g/ 8 g/ +16 g Digital Accelerometer", XP055646542, Jan. 2015, https://www.analog.com/media/en/technical-documentation/data-sheets/ADXL345.pdf.

International Search Report (PCT/ISA/210) and Written Opinion (PCT/ISA/237) dated Dec. 5, 2019, by the European Patent Office as the International Searching Authority for International Application No. PCT/EP2019/074151.

* cited by examiner

DUAL-MODULE MOTION DETECTION SYSTEM FOR THE POWER SAVING OF RATE ADAPTION ALGORITHM IN LEADLESS PACEMAKER

CROSS-REFERENCE TO RELATED APPLICATIONS

This application is the United States national phase under 35 U.S.C. § 371 of PCT International Patent Application No. PCT/EP2019/074151, filed on Sep. 11, 2019, which claims the benefit of U.S. Patent Application No. 62/752,384, filed on Oct. 30, 2018, the disclosures of which are hereby incorporated by reference herein in their entireties.

TECHNICAL FIELD

The present invention relates to an implantable cardiac pacemaker, particularly in the form of an implantable leadless pacemaker, that comprises a motion detection system.

BACKGROUND

The normal heart rate of a human being fluctuates during the course of 24 hours depending upon his/her activity. During sleep, the heart rate normally slows. During times of activity or stress, however, the heart rate normally speeds up to meet the associated higher metabolic requirements. Individuals with an abnormality of the conduction system of the heart may be unable to properly speed up the heart rate during activity or stress. This can result in fatigue, shortness of breath, and/or activity intolerance.

Pacemakers with rate adaptation comprise one or more sensors built into the pulse generator that can sense increasing activity. The sensor(s) will automatically increase or decrease the heart rate according to the body's needs.

Presently, temperature based rate adaptation, pH based rate adaptation, and traditional motion sensor based rate adaptation schemes are used in pacemakers.

Particularly, the temperature-based rate adaptation has a relatively slow response which can be disadvantageous when fast changes must be detected. Also, some health issues such as the flu can result in the increase of body temperature, which can cause a false positive rate response.

Further, pH based rate adaptation has special requirements for the electrode's electro-chemical property. Often, materials which fulfil the requirements are not biocompatible or suitable for long term implantation. In addition, there can be potential unpredicted performance due to inflammation and encapsulation of the electrode. Also, pH of the blood can be subtly changed by taking medicines.

Furthermore, traditional pacemakers use accelerometers in the can of the pacemaker to detect physical activities, which are in turn used to adapt the pacing rate. Presently, the motion detection system for an activity-based rate adaptation algorithm in a conventional pacemaker runs continuously. The detected motion signal is used to calculate the target pacing rate. When the pacemaker-dependent patient is active, motion will be detected by the system, generating a higher target heart rate. Then the pacemaker will adapt the pacing rate towards the target heart rate in order to meet the metabolic demand of the patient. The motion detection system runs continuously so the physical activity signals won't be missed meeting the patient's increased metabolic demands due to the activity. However, the high current consumption of the activity-based rate adaptation module and continuous use and powering of an accelerometer curtails the service life of a pacemaker, particularly leadless pacemaker.

Most of the time, however, patients are not so active that the basic pacing rate cannot support the demand. So the operating current of the motion detection system during this time is wasted. Particularly, with regard to battery capacity, unnecessary current consumption should be avoided.

U.S. Publication No. 2004/0116819 A1 discloses an implanted device-implemented method of detecting and monitoring congestive heart failure in a patient which includes performing ongoing measurements of changes in local impedance of a portion of the patient's body between at least two electrodes on the exterior of the implanted device, the changes representing ventilation of the patient, and including measuring the patient's respiratory rate and respiratory amplitude. A body-implantable device is adapted to detect and monitor congestive heart failure in a patient, and includes a circuit module coupled to plural surface electrodes of the device arranged and adapted, when the device is implanted, for contacting tissue in a portion of the patient's body generally occupied by the lungs, to monitor changes in local impedance of said body portion, and to detect the patient's EKG.

The present disclosure is directed toward overcoming one or more of the above-mentioned problems, though not necessarily limited to embodiments that do.

SUMMARY

It is an object to provide energy-efficient rate adaptation technology for a pacemaker. It is desirable to have a motion detection system in a pacemaker that conserves energy by efficiently controlling the operating states of an activity-based rate adaptation unit partitioned into sub-units of functionality.

An implantable cardiac pacemaker according to claim 1 is disclosed. Further embodiments are subject matter of dependent claims.

In one aspect, an implantable cardiac pacemaker is provided. The pacemaker is configured to apply pacing pulses to the heart of a person during operation of the pacemaker. The pacemaker comprises a motion detection system that comprises a first module and a second module. The first module is configured to continuously run during operation of the pacemaker. The second module is configured to receive a trigger signal to change the second module from an idle state to an active state or to receive a further trigger signal to change the second module from an active state to an idle state. Energy consumption per time unit of the second module in the active state is larger than in the idle state. When the second module is in its active state, the second module is configured to execute a rate adaptation algorithm that adapts a rate of the pacing pulses to meet a metabolic demand of the person.

The motion detection system may further comprise an intermediate processor. The first module may be configured to communicate with the second module via the intermediate processor.

In one embodiment, an implantable cardiac pacemaker is provided which is configured to apply pacing pulses to the heart of a person during operation of the pacemaker. The pacemaker comprises a motion detection system that comprises a first module and a second module, wherein the first module is configured to continuously run during operation of the cardiac pacemaker, and wherein the first module is configured to send a trigger signal to the second module to change the second module from an idle state to an active state or to send a further trigger signal to the second module to change the second module from an active state to an idle state. Energy consumption per time unit of the second module in the active state is larger than in the idle state. When the second module is in its active state, the second module is configured to execute a rate adaptation algorithm that adapts a rate of the pacing pulses to meet a metabolic demand of the person.

The first module may be configured to send the trigger signal and/or the further trigger signal to the second module, e.g. via the intermediate processor. Alternatively or in addition, the intermediate processor may be configured to send the trigger signal and/or the further trigger signal to the second module.

According to survey/clinical studies (American Heart Association Recommendations for Physical Activity in Adults, (https://www.heart.org/en/healthy-living/fitness/fitness-basics/aha-recs-for-physical-activity-in-adults)), the daily exercise time in the clinical population is less than 1 hour. In other words, only in 1 hour out of 24 hours does the pacemaker need to increase the rate of the heart to support the higher metabolic requirements due to physical activities. However, in present pacemakers, the motion detection system, which is used to support a rate adaptation algorithm, is fully operational at all times. The energy consumption of the motion detection system is unnecessary most of the time.

Particularly, an implantable leadless pacemaker (ILP) has a very strict power consumption requirement, which presents a challenge for the realization of conventional activity-based rate adaptation implementation using continuously running motion information processing. Therefore, the present invention particularly suggests a dual-module strategy to meet the tight power requirement of rate responsive pacing in a cardiac pacemaker, particularly in a leadless pacemaker.

Unlike traditional motion sensors, the proposed motion detection system preferably has two separated modules: a continuously running first module, which particularly may contain mostly analog components and consumes a low current; and an on-demand running second module, which particularly contains the processor and supporting logics, and consumes most of the system power. A module is a collection of circuits and/or programmable instruction units.

Particularly, the first module is running continuously to detect the analog motion signals in the background. On the other hand, the second module is preferably only active by a trigger from an event of physical activity of the person in which the pacemaker is implanted and/or the expiration of a pre-defined timer. Then, the second module returns to the idle state when the trigger has been serviced and does not reoccur. Given the actual time for activities of daily living, the second module will be off most of the time for the average pacemaker patient.

When the processor of the second module is turned off in a motion detection system, such as a hardware accelerator (a dedicated digital block to process analog motion data and calculate a target heart rate), the power consumption can be decreased to $1/10$ or even lower. Thus, with the proposed dual-module strategy, the current consumption can be decreased by 30%~90% compared to traditional activity-based rate adaptation implementation using the continuously running motion sensors.

Particularly, according to an embodiment, an implantable leadless pacemaker (ILP) may comprise a hermetically sealed housing enclosing a pulse generator for generating said pacing pulses and a battery for supplying energy to the pulse generator. The leadless pacemaker may further comprise fastening means provided on the distal end of the housing for fastening the leadless pacemaker to the heart of the person (e.g. in the ventricle or in the atrium). The leadless pacemaker may further comprise a pair of electrodes (e.g. a cathode and an anode) to apply the electrical stimulation in form of the pacing pulses to the heart of the person and to allow sensing: the pacing electrode may be located at a distal end of the housing of the leadless pacemaker and in contact with endocardial tissue; the returning electrode may be located at the proximal end of the housing. Regarding such pacemaker, the notion leadless means that the electrodes of the implantable leadless pacemaker are directly connected to the pulse generator enclosed in the housing and mechanically attached to the housing of the leadless pacemaker, thus an external lead is not necessary.

Further, according to an embodiment of the implantable cardiac pacemaker, the first module is configured to send said trigger signal to the second module to change the second module from the idle state to the active state in case a physical activity of the person is detected by the first module and/or each time a pre-defined time span expires. The first module and the second module may exchange several signals, including a motion signal, a voltage signal, an acceleration signal, and/or a timing signal.

Furthermore, according to an embodiment of the implantable cardiac pacemaker, the second module is in the idle state by default, only activated by said trigger signal sent from the first module and/or the intermediate processor, and configured to return from the active to the idle state after expiration of a pre-defined time span during which no activating trigger signal has been sent by the first module and/or the intermediate processor to the second module.

Further, according to an embodiment of the implantable cardiac pacemaker, the first module comprises a motion sensor, particularly a 3-axis transducer, configured to detect a physical activity of the person, wherein the motion sensor is configured to generate a motion signal indicative of said physical activity or of a posture of the person.

Furthermore, in an embodiment, the first module comprises a current-to-voltage converter that is configured to convert a current signal of the motion sensor to a voltage signal. Particularly, the first module can comprise a filter configured to filter the voltage signal.

Further, according to an embodiment, the first module comprises a trigger activation component that is configured to generate the trigger signal based on said (e.g. filtered) voltage signal.

Particularly, according to an embodiment of the implantable cardiac pacemaker, the second component comprises a host processor for carrying out said rate adaptation algorithm, wherein said trigger signal for changing the second module from the idle state to the active state can be an interrupt that is sent to the host processor by the first module, particularly by the trigger activation component.

Further, according to an embodiment of the implantable cardiac pacemaker, the first module (particularly the trigger activation component) is configured to send said trigger signal to the second module to change the second module from the idle state to the active state in case an amplitude of the motion signal generated by the motion sensor exceeds a pre-defined threshold.

According to a further embodiment of the implantable cardiac pacemaker, the first module is configured to send said trigger signal to the second module to change the second module from the idle state to the active state in case a spectral property of the motion signal generated by the motion sensor crosses (e.g. exceeds) a pre-defined threshold in a frequency range.

Further, according to an embodiment of the implantable cardiac pacemaker, the first module is configured to send said trigger signal to the second module to change the second module from the idle state to the active state in case a difference between the motion signal and a reference level of the motion signal exceeds a threshold. Particularly, the reference level can be a portion of the average amplitude of the motion signal tracked over time (e.g. daily), which can represent the baseline motion when the patients are not in a state of increased metabolic demand (e.g. in exercise).

Further, according to an embodiment of the implantable cardiac pacemaker, the first module is configured to determine a posture of the person based on the motion signal (which particularly represents accelerations of the person along three orthogonal axes which allow to determine a current posture of the person), wherein the first module is configured to send said further trigger signal to the second module to change the second module from the active state to the idle state in case the determined posture of the person corresponds to a horizontal position of the person that has lasted for a pre-defined time span.

Further, according to an embodiment of the implantable cardiac pacemaker, the first module is configured to send said further trigger signal to the second module to change the second module from the active state to the idle state in case a pre-defined sleeping time starts or low activity-period of the person has lasted for a certain period.

Further, according to an embodiment of the implantable cardiac pacemaker, the first module and/or the intermediate processor are configured to alternately send said trigger signal and said further trigger signal to the second module to alternately have the second module in the active state for a first time span and in the idle state for a second time span.

Further, according to an embodiment of the implantable cardiac pacemaker, the first module is configured to increase the second time span in case the second module does not receive said trigger signal indicating a physical activity of the person during a pre-defined time span, and/or wherein the first module is configured to decrease the second time span in case the second module receives said trigger signal indicating a physical activity of the person.

Further, according to an embodiment of the implantable cardiac pacemaker, when an amplitude of the motion signal is below a pre-defined threshold, the second module is configured to be in its idle state, and wherein when the amplitude of the motion signal is above the threshold, the first module is configured to alternately send said trigger signal and said further trigger signal to the second module to alternately keep the second module in the active state for a first time span and in the idle state for a second time span.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, embodiments, further features and advantages of the present invention are described with reference to the Figures, wherein.

DETAILED DESCRIPTION

Figure 1:
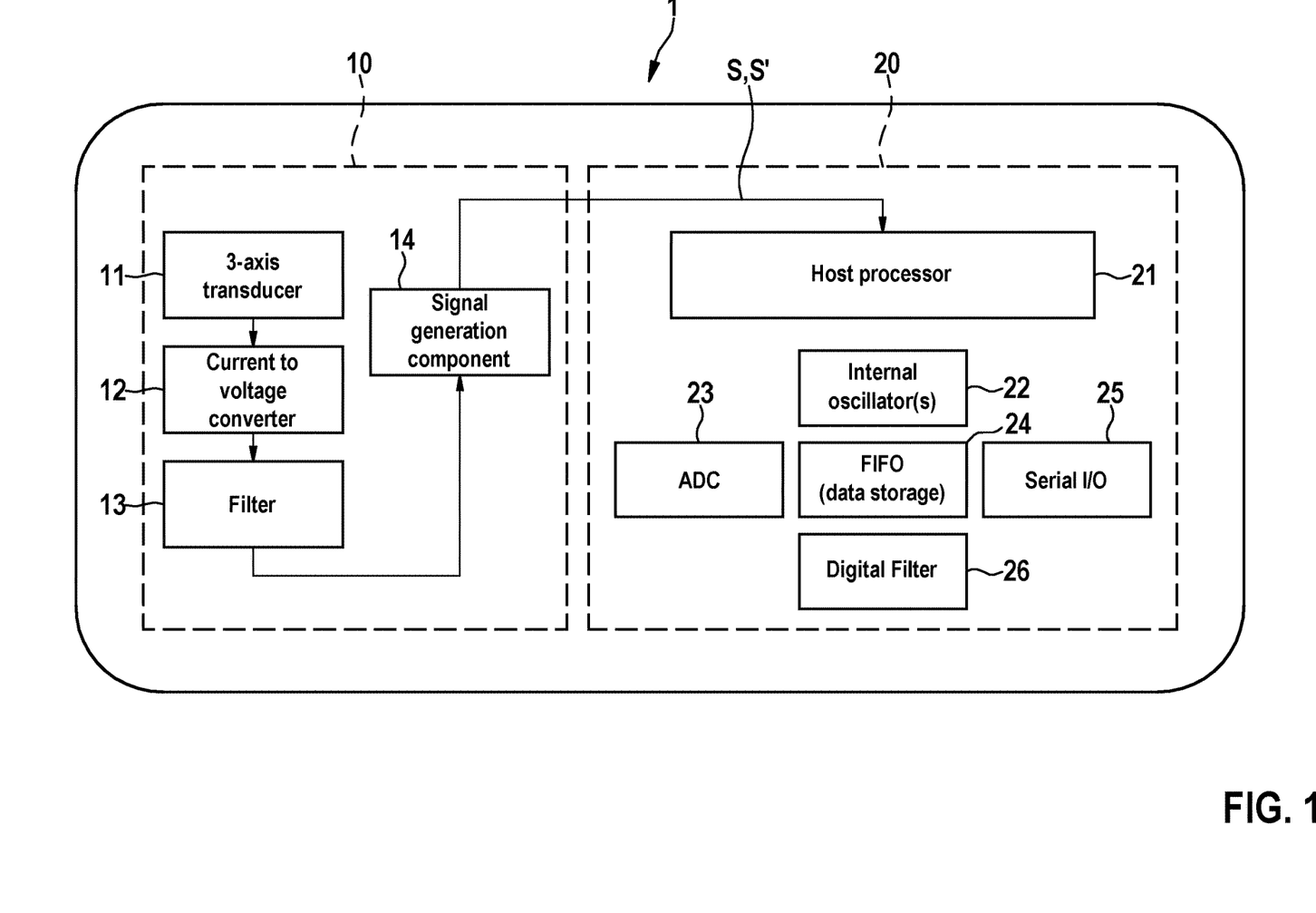
FIG. 1 shows a schematic illustration of an embodiment of an implantable cardiac pacemaker comprising a modularized motion detection system.

FIG. 1 shows a schematic illustration of an embodiment of an implantable cardiac pacemaker according to the present invention. Particularly, the pacemaker is an implantable leadless pacemaker. Particularly, the pacemaker 1 is configured to apply pacing pulses to the heart of a person during operation of the pacemaker 1 using a pulse generator and an electrode which are not shown in FIG. 1. Further, the pacemaker 1 comprises a motion detection system that comprises a first module 10 and a second module 20, wherein the first module 10 is configured to continuously run during operation of the pacemaker 1, and wherein the first module 10 is configured to send a trigger signals S to the second module 20 to change the second module 20 from an idle state to an active state or to send a further trigger signal S' to the second module 20 to change the second module 20 from an active state to an idle state, wherein an energy consumption per time unit of the second module 20 in the active state is considerably larger than in the idle state, and wherein when the second module 20 is in its active state, the second module 20 is configured to execute a rate adaptation algorithm that adapts a rate of the pacing pulses to meet a metabolic demand of the person.

The continuously running first module 10 particularly contains mostly analog components and consumes a small portion of the power (e.g. 10% or even less) of the pacemaker 1. On the other hand, the on-demand running second module 20 contains a processor 21 for conducting the rate adaptation algorithm and supporting logic, which consumes a significant amount of power when active.

Particularly, the second module 20 further comprises internal oscillators 22, an analog-to-digital converter (ADC) 23, a data storage (e.g. FIFO) 24, a serial I/O 25, and a digital filter 26. When the motion signal of a physical activity is detected, the second module 20 receives said trigger signal and switches to the active state. The motion signal from the motion sensor transducer in the first module 10 is used to adapt the pacing rate to meet the metabolic requirement of the patient. First, the analog motion signals are converted to digital data via ADC 23. The digital signal is then filtered by the digital filter 26, whose bandwidth is corresponding with the frequency spectrum of the activity signals. Then the energy of the filtered signals is calculated and output to other modules of the leadless pacemaker to support activity-based rate adaptation via serial I/O 25. The signals at each step can be stored in FIFO 24, if necessary.

It is particularly proposed to keep the second module 20 off (e.g. idle state) by default and only turn it on (e.g. active state) when there is demand to support the rate adaptation algorithm in the pacemaker 1.

Particularly, the first module 10, which can contain a motion sensor (e.g. a 3-axis transducer) 11, a current to voltage converter 12, a filter 13, and a trigger activation component 14, is continuously running. The trigger activation component 14 is particularly used to determine when the second module 20 will be running. Depending on the types of trigger signals, the trigger activation component 14 can be of several alternative designs. The detailed information regarding different types of the triggers will be explained below. As an example, if the trigger activation component 14 is designed to detect motion amplitude, when a large motion signal is detected, indicating that the patient (i.e. the person in which the pacemaker 1 is implanted) is starting to experience increased metabolic demand (e.g. during exercise) and requires higher pacing rate to meet the increased metabolic demand, the trigger activation component 14 will send a trigger signal S (i.e., an interrupt S) to the host processor 21 and wake up the second module 20. Then, the components in the second module 20 will run to support a means of rate adaptation. Particularly, the second module 20 will only run when the trigger signals S are active; and then change back to an energy conversing state, such as, idle, standby, suspended, sleep, or off mode.

Several types of triggers are described in the following. The trigger types described in the following paragraphs include both S (trigger signal to change the second module 20 from an idle state to an active state) and S' (further trigger signal to change the second module 20 back to an idle state from an active state). The timing related trigger signals (duty-cycling, preset time span, etc.) are provided by the intermediate processor, which may or may not need support from the detection of the first module. The further trigger signal S' (change the second module back to an idle state) may include: 1) the expiration of a pre-defined time span in which no trigger signal S (amplitude threshold, spectral threshold, delta) is sent by the first module; 2) the expiration of a preset time of duty-cycling; 3) posture change (e.g. horizontal posture for a certain time; and 4) pre-defined time window by the users.

Motion amplitude threshold: When the patient starts to experience increased metabolic demand (e.g. starts exercise), much larger motion signals will be detected by the first module 10. Thus, the trigger activation module 14 can be implemented using an amplitude comparator. A motion signal, which is above a resting motion amplitude and below an exercising motion amplitude, is evaluated against a threshold. When the motion amplitude is below the threshold, the second module 20 is kept in the idle state as default. When the motion amplitude exceeds the threshold, the trigger S will activate the second module 20. On the other hand, when the detected motion signals have been below the threshold for a certain time, the second module 20 will be turned off (e.g. idle state) again to save the power consumption. Off is understood to stand for the alternative states, such as, suspended or sleep as applicable and is also denoted as idle state herein.

Spectral power threshold: Most of the activity signals are in the frequency range of 2 Hz to 6 Hz. Thus, using a spectral power threshold is another type of trigger to activate the second module 20. Other non-activity motion signals normally have different spectra. For instance, driving has most frequency components higher than 10 Hz, while breathing motion is normally lower than 1 Hz. When the power is in the frequency range of interest (e.g. 2 Hz to 6 Hz) or exceeds a threshold, the second module 20 will be activated to support the rate adaptation.

Delta in acceleration signals (Jerk): Instead of detecting the absolute amplitude of acceleration or the signal spectrum, the trigger can be activated when there is a sudden change of the signals. For example, the delta of acceleration (Jerk) may be used as a trigger, though other derivatives, integrations, or statistical properties of acceleration may be used. The trend of the signals would be tracked over time with respect to a reference (and other references may also be used). A large change of the signal from the reference indicates that the patient is starting physical activity and the second module 20 will be turned on to support rate adaptation algorithm.

Posture trigger: The acceleration signals detected by the first module 10 are able to indicate the posture of the patient. When the patients are in the standing position for a sufficient time, the second module 20 can be turned on (e.g. active state) to be ready for rate response support for the patients. When the patients are in the horizontal position for a relative long time (saying longer than 1 hour), the patients are most likely in sleep, and there is a small chance that the patients will be in a state of increased metabolic demand (e.g. an exercise state) before changing to sitting or standing posture. Thus, the second module 20 can be turned off (e.g. idle state) after a patient is in lying-down position for a relative long time.

Circadian timing trigger: Based on the understanding of the settled routine of the patient, the second module 20 can be turned on (e.g. active state) during the mostly active period and off (e.g. idle state) during the sleeping time and other low-activity periods.

Duty-cycling preset timer trigger: In traditional activity-based rate adaptation algorithm, the proposed pacing rate is updated every second based on the average motion signals. When the duty cycling strategy is applied, the second module 20 is turned on for a certain (first) time span, and then turned off (e.g. idle state) for another (second) time span. In this scenario, the trigger to activate the second module 20 can be a monostable timing control by the intermediate processor. At the end of the off (e.g. idle state) period, the timer will activate the trigger to switch on the second module 20. The power saving rate depends on the selection of the on and off periods. With the duty-cycling strategy, although the response time of the rate adaptation means is extended from one second to several seconds, it is still clinically accepted and won't significantly affect the performance of rate adaptation.

Dynamic duty-cycling preset timer trigger: Similar to duty-cycling preset time trigger, a preset timer will be used as the trigger to activate the second module 20. However, in most of the time, the patients are not in a state of increased metabolic demand, so the off-period of the duty-cycling will be set longer to save more energy. On the other hand, when physical motion of the patient is detected, the off-period will be shortened to decrease the response time of the rate adaptation algorithm. Considering that the average exercise time for the clinical population is only 1 hour per day, the dynamic duty-cycling will decrease the power usage significantly. The advantage to this approach is to allow different duty-cycling based on the discrimination between patients' status, i.e., at rest or in a state of increased metabolic demand (e.g. physical exercise), to maximize the saving of power.

Combined threshold and duty-cycling trigger: When the motion signals are below the threshold, the second module 20 of the system will be completely off (e.g. idle state). When the patients are in a state of increased metabolic demand (e.g. exercise) and the motion signals are above the threshold, the second module 20 will be turned on based on the pre-set duty-cycling timing The trigger signal in this case will be the combination of the above-threshold trigger from module 10 and the timing control from the intermediate processor. In this way, the energy saving will be even more effective.

User-defined/programmed trigger: The second module 20 can be also switched between idle and active states by user-defined or programmed trigger signal, for example, a certain pattern of posture changes.

Different trigger signals can be combined to control the state of the second module 20. For instance, the second module 20 can be turned on (e.g. active state) by the S of delta in acceleration signals, and turned back to idle state by the S' of amplitude threshold, posture, or preset time span.

The dual-mode of the motion sensor can be programmable to be enabled or disabled. When this feature is disabled, the motion sensor is working identical to the traditional motion sensor, which is turned on to support the rate response continuously.

Based on an investigation of digitized accelerations, the power consumption can be decreased by 90% or even more when the primary processor 21 inside the sensor is powered off. Therefore, turning off the second module 20, including the processor 21, oscillator 22, ADC 23, interface 25, and/or data storage buffer 24 when the patients are not in a state of increased metabolic demand can save the power usage by 60%~90%.

Using the above described motion amplitude threshold, the spectral density threshold or the delta in acceleration signals, the second module 20 will only run when the physical motion signals from the state of increased metabolic demand (e.g. exercise) are detected. Based on the literature and surveys, the average exercise time is only 1 hour daily. Therefore, for most of the time, the motion detection system 10, 11 can save up to 90% power. On the other hand, the trigger activation module 14 will wake up the second module 20 to support a rate adaptation algorithm once motion signals are detected. Therefore, the performance of a rate adaptation algorithm won't be affected by this strategy.

Using the above described posture trigger or circadian timing trigger, the second module 20 will be turned off when the patients are in sleep. Comparing to the other triggers described above, the posture trigger or the circadian timing trigger do not provide a power saving rate of similar magnitude, however, the detection of the posture and circadian timing triggers is simple and stable. Considering that the sleeping time for normal humans is around ⅓ each day, the power can be saved as much as 30%.

The above described duty-cycling preset timer trigger and the dynamic duty-cycling preset timer trigger are based on the user preset timer and are easy to implement. Considering a duty cycling of ⅕, in which the second module 20 is turned on for a time t1, and off for 4*t1, the power usage can be decreased by 80%. In a traditional pacemaker, the target pacing rate is updated every 1 second. When the ⅕ duty cycling is applied, the response time increases from 1 second to 5 second, which is still clinically acceptable. In addition, considering the frequency spectrum of [2 Hz-6 Hz] of the activity signals, the turning on period t1 can be decreased to 0.5 second (2 Hz) and still covers motion signal cycles. In this case, the overall rate adaptation response time using the duty cycle of ⅕ will be as short as 2.5 second, while the power saving rate is as high as 80%. When the dynamic duty cycling is applied, a shorter "on time" duty cycling will be applied when the patient is not exercising in most of the day and the power saving can be even more significant.

Finally, the combined threshold and duty-cycling trigger uses a combination of the duty-cycling strategy and the motion threshold based trigger. Here, the second module 20 will be completely off when there are no motion signals detected and turned on ⅕ of the time when the motion signals exist. Assume that the patient exercises for 3 hours per day, which is 200% more than the average exercise time, the overall power consumption using (h) will be only 11% of the conventional motion detection system.

Figure 2:
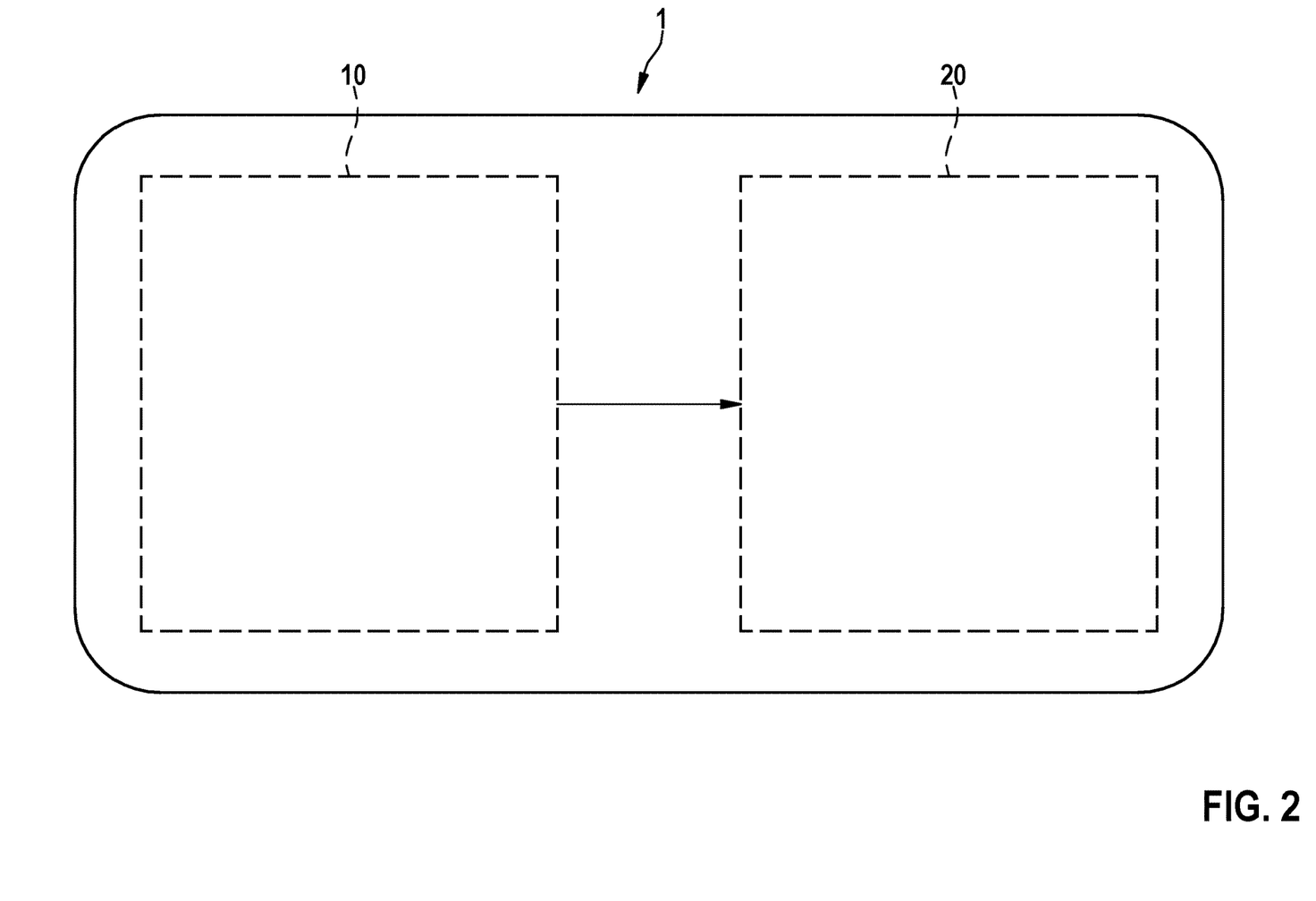
FIG. 2 shows a schematic illustration of an embodiment of an implantable cardiac pacemaker wherein a modularized motion detection system is implemented as a direct-control and/or asynchronous system comprising two modules.

FIG. 2 shows an embodiment of an implantable cardiac pacemaker, wherein a modularized motion detection system is implemented as two modules in a direct-control and/or asynchronous system. The first module 10 communicates directly with the second module 20. The direct system has a simple system design with the direct interface between the first module 10 and the second module 20.

Figure 3:
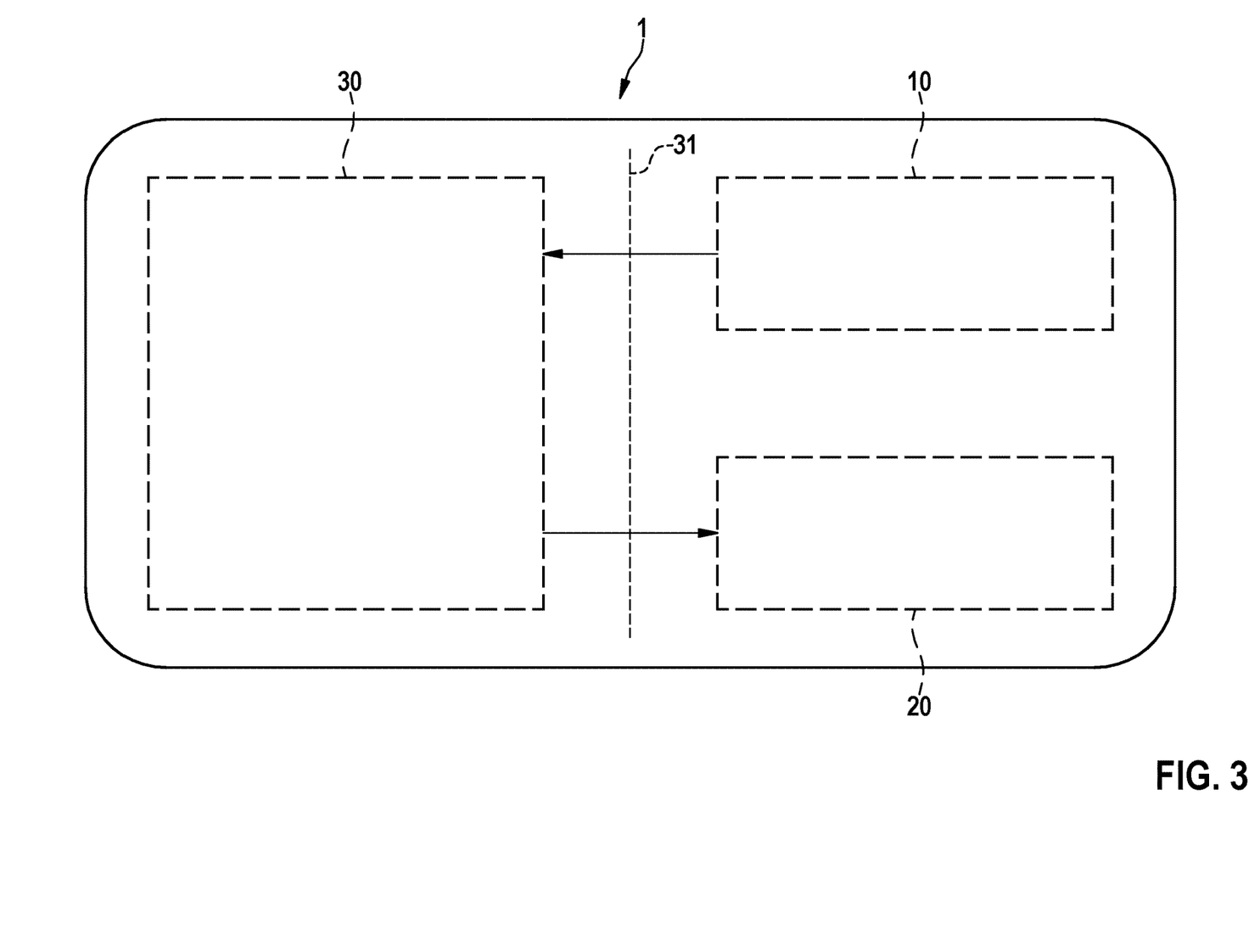
FIG. 3 shows a schematic illustration of an embodiment of an implantable cardiac pacemaker wherein a modularized motion detection system is implemented as a synchronous system comprising two modules.

FIG. 3 shows another embodiment of an implantable cardiac pacemaker, wherein a modularized motion detection system is implemented as a synchronous system. The first module 10 communicates via an intermediate processor 30 with the second module 20. Communication between the first module 10 and the intermediate processor 30 as well as communication between the intermediate processor 30 and the second module 20 is performed via a control/data interface or bus 31. The synchronized system may provide the capability of creating more complicated trigger signals to switch on/off the second module 20.

Summarizing, the present invention supports activity-based and/or cardiac motion based rate adaptation in pacemakers, particularly leadless pacemakers.

Advantageously, the power consumption can be decreased by 30%-90% comparing to the current motion detection system for a rate adaptation algorithm, which can help to meet the tight current consumption requirement for certain pacemakers such as leadless pacemakers.

Figure 4:
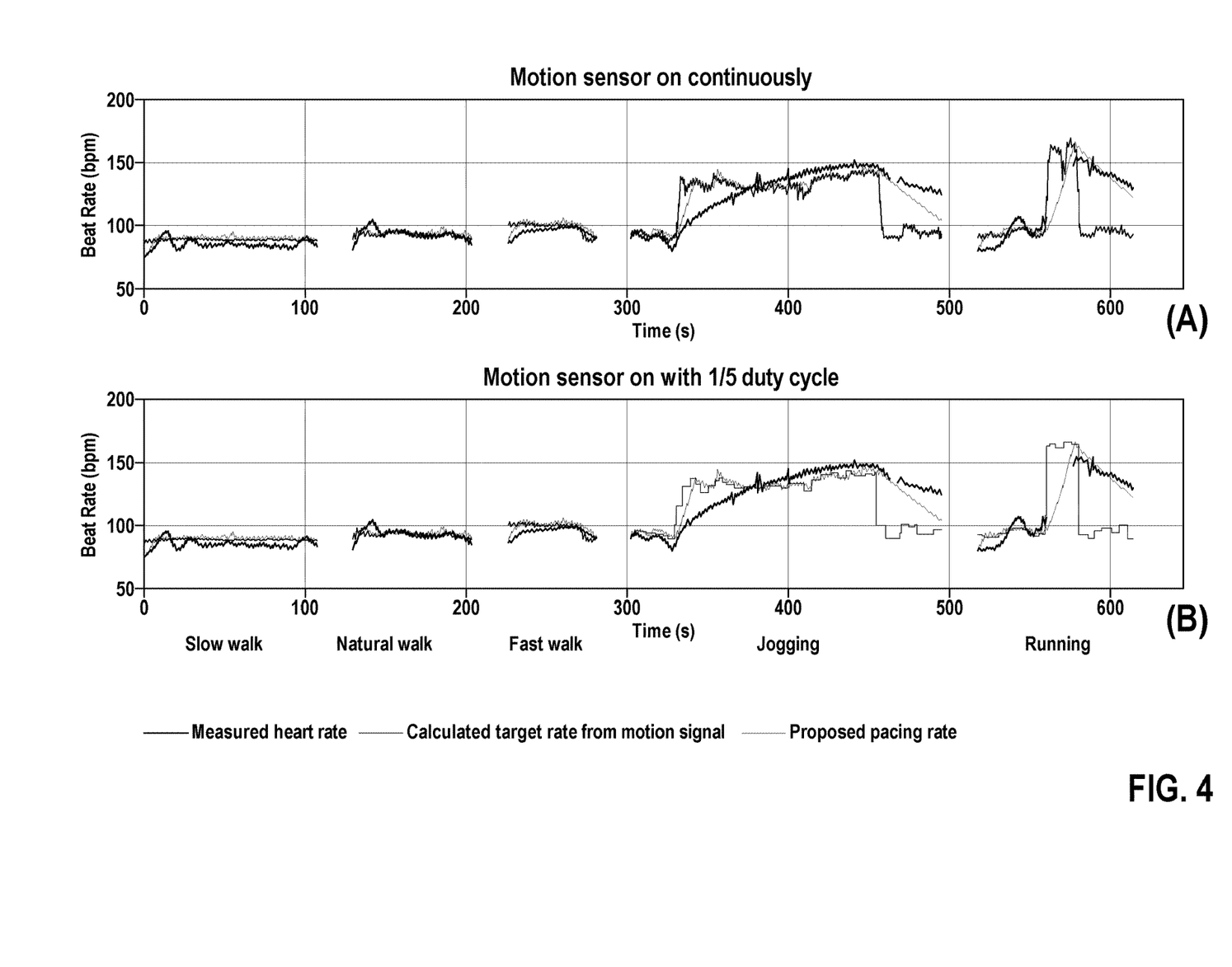
FIG. 4 shows a pacing rate from a rate adaptation algorithm executed by a cardiac pacemaker, when the motion detection system is (A) continuously on and (B) only turned on with a duty cycle of ⅕.

Furthermore, the performance of the rate adaptation algorithm will not be affected. An example for this feature is illustrated in FIG. 4. Here, the second module 20 is turned on with a duty cycle, the performance of the rate adaptation is not affected. As shown in FIG. 4, the output pacing rate from rate adaptation algorithm is very similar when the motion detection system is (A) continuously on and (B) only turned on with a duty cycle of ⅕.

Further, the present invention supports multiple options in the design of the trigger activation component 14 which is used to turn on the second module 20 when there is a demand of increasing pacing rate. Finally, the present invention supports the discrimination of different types of activity.

It should be understood that the designation of the first module 10 and the second module 20 while predominantly analog and digital, respectively, other embodiments of this invention may contain modules of mixed analog/digital or exchanged functionality to optimize power savings in the continuously running and idle modules.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable cardiac pacemaker, wherein the pacemaker is configured to apply pacing pulses to the heart of a person during operation of the pacemaker, and wherein the pacemaker comprises a motion detection system that comprises a first module and a second module, wherein the first module is configured to continuously run during operation of the pacemaker, and wherein the second module is configured to receive a trigger signal to change the second module from an idle state to an active state or to receive a further trigger signal to change the second module from an active state to an idle state, wherein an energy consumption per time unit of the second module in the active state is larger than in the idle state, and wherein when the second module is in its active state, the second module is configured to execute a rate adaptation algorithm that adapts a rate of the pacing pulses to meet a metabolic demand of the person; wherein the first module is configured to send said trigger signal to the second module to change the second module from the idle state to the active state or to send said further trigger signal to the second module to change the second module from the active state to the idle state.

2. The implantable cardiac pacemaker according to claim 1, wherein the motion detection system further comprises an intermediate processor, wherein the intermediate processor is configured to send said trigger signal to the second module to change the second module from the idle state to the active state or to send said further trigger signal to the second module to change the second module from the active state to the idle state.

3. The implantable cardiac pacemaker according to claim 1, wherein the first module comprises a motion sensor, particularly a 3-axis transducer, configured to detect a physical activity of the person, wherein the motion sensor is configured to generate a motion signal indicative of said physical activity.

4. The implantable cardiac pacemaker according to claim 3, wherein the first module comprises a current-to-voltage converter that is configured to convert a current signal of the motion sensor to a voltage signal.

5. The implantable cardiac pacemaker according to claim 4, wherein the first module comprises a filter configured to filter the voltage signal.

6. The implantable cardiac pacemaker according to claim 4, wherein the first module comprises a trigger activation component that is configured to generate the trigger signal based on said voltage signal.

7. The implantable cardiac pacemaker according to claim 3, wherein the first module is configured to send said trigger signal to the second module to change the second module from the idle state to the active state when an amplitude of the motion signal generated by the motion sensor exceeds a pre-defined threshold.

8. The implantable cardiac pacemaker according to claim 3, wherein the first module is configured to send said trigger signal to the second module to change the second module from the idle state to the active state when a spectral density of the motion signal generated by the motion sensor exceeds a pre-defined threshold in a predefined frequency range.

9. The implantable cardiac pacemaker according to claim 3, wherein the first module is configured to send said trigger signal to the second module to change the second module from the idle state to the active state when a difference between the motion signal and a reference level of the motion signal exceeds a pre-determined threshold.

10. The implantable cardiac pacemaker according to claim 3, wherein the first module is configured to determine a posture of the person based on the motion signal, wherein the first module is configured to send said further trigger signal to the second module to change the second module from the active state to the idle state when the determined posture of the person corresponds to a horizontal position of the person in which the person has been for a pre-defined time span.

11. The implantable cardiac pacemaker according to claim 3, wherein when an amplitude of the motion signal is below a pre-defined threshold, the second module is in its idle state, and wherein when the amplitude of the motion signal is above the threshold, the first module is configured to alternately send said trigger signal and said further trigger signal to the second module to alternately keep the second module in the active state for a first time span and in the idle state for a second time span.

12. The implantable cardiac pacemaker according to claim 1, wherein the first module is configured to send said further trigger signal to the second module to change the second module from the active state to the idle state when a pre-defined sleeping time or low activity-period of the person starts.

13. The implantable cardiac pacemaker according to claim 1, wherein the second module is configured to alternate between the active state for a first time span and the idle state for a second time span, wherein the second module changes between idle state and the active state based on a timing control, which is preset and programmable in the first module.

14. The implantable cardiac pacemaker according to claim 13, wherein the second time span is increased when the motion sensor does not detect a physical activity of the person during a pre-defined time span, and/or wherein the second time span is decreased when the motion sensor detects a physical activity of the person.

* * * * *